(12) United States Patent
Novak et al.

(10) Patent No.: US 9,534,236 B2
(45) Date of Patent: Jan. 3, 2017

(54) MEMBRANES FOR WASTEWATER-GENERATED ENERGY AND GAS

(71) Applicant: Regents of the University of Minnesota, Minneapolis, MN (US)

(72) Inventors: Paige J. Novak, St. Paul, MN (US); William A. Arnold, Minnetonka, MN (US); Erin M. Surdo, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/198,104

(22) Filed: Mar. 5, 2014

(65) Prior Publication Data

US 2014/0256007 A1    Sep. 11, 2014

Related U.S. Application Data

(60) Provisional application No. 61/774,857, filed on Mar. 8, 2013.

(51) Int. Cl.
| | |
|---|---|
| *C02F 3/28* | (2006.01) |
| *C12P 3/00* | (2006.01) |
| *C12M 1/12* | (2006.01) |
| *C12M 1/107* | (2006.01) |
| *C12M 1/00* | (2006.01) |

(Continued)

(52) U.S. Cl.
CPC .................. *C12P 3/00* (2013.01); *C02F 3/102* (2013.01); *C12M 21/04* (2013.01); *C12M 23/20* (2013.01); *C12M 23/40* (2013.01); *C12M 25/10* (2013.01); *C12N 11/08* (2013.01); *C12P 5/023* (2013.01); *Y02E 50/343* (2013.01); *Y02W 10/15* (2015.05)

(58) Field of Classification Search
CPC ........ C12M 25/10; C12M 21/04; C12N 11/08; C12P 3/00
See application file for complete search history.

(56) References Cited

U.S. PATENT DOCUMENTS

| | | |
|---|---|---|
| 4,148,689 A | 4/1979 | Hino et al. |
| 4,391,909 A | 7/1983 | Lim |

(Continued)

FOREIGN PATENT DOCUMENTS

| | | |
|---|---|---|
| CN | 1715182SA | 1/2006 |
| WO | WO-02/10218 A1 | 2/2002 |

(Continued)

OTHER PUBLICATIONS

"U.S. Appl. No. 14/001,094, Response filed Nov. 12, 2015 to Restriction Requirement mailed Sep. 17, 2015", 9 pgs.

(Continued)

*Primary Examiner* — Jonathan Hurst
(74) *Attorney, Agent, or Firm* — Schwegman Lundberg & Woessner, P.A.

(57) ABSTRACT

An example includes an apparatus, method, and system for producing and extracting a gas from a wastewater fluid. The apparatus can include a membrane including at least one hollow fiber, the at least one hollow fiber configured to convey a gas extracted from a wastewater fluid. Bacteria can be immobilized within the membrane, and the bacteria configured to produce the gas during treatment of the wastewater fluid.

10 Claims, 6 Drawing Sheets

(51) Int. Cl.
  *C12N 11/08* (2006.01)
  *C12P 5/02* (2006.01)
  *C02F 3/10* (2006.01)

(56) References Cited

U.S. PATENT DOCUMENTS

| | | | |
|---|---|---|---|
| 5,200,334 A | 4/1993 | Dunn et al. | |
| 5,229,096 A | 7/1993 | Cohen | |
| 5,252,318 A | 10/1993 | Joshi et al. | |
| 5,416,022 A * | 5/1995 | Amiot | B01D 63/00 435/297.2 |
| 5,508,193 A | 4/1996 | Mandelbaum et al. | |
| 5,693,513 A | 12/1997 | Pope | |
| 5,739,020 A | 4/1998 | Pope | |
| 6,214,593 B1 | 4/2001 | Carturan et al. | |
| 6,248,321 B1 | 6/2001 | Winder et al. | |
| 6,284,522 B1 | 9/2001 | Wackett et al. | |
| 6,303,290 B1 | 10/2001 | Liu | |
| 6,369,299 B1 | 4/2002 | Sadowsky et al. | |
| 6,495,352 B1 | 12/2002 | Brinker et al. | |
| 6,673,582 B2 | 1/2004 | McTavish | |
| 6,825,001 B2 | 11/2004 | Wackett et al. | |
| 6,979,464 B2 | 12/2005 | Gutowska | |
| 7,033,571 B2 | 4/2006 | Gutowska et al. | |
| 7,052,913 B2 | 5/2006 | Babich et al. | |
| 7,204,997 B2 | 4/2007 | Bromberg et al. | |
| 7,510,656 B2 | 3/2009 | Shafer et al. | |
| 8,337,923 B2 | 12/2012 | Coyne et al. | |
| 8,367,109 B2 | 2/2013 | Chidambaram et al. | |
| 2001/0055797 A1 | 12/2001 | Conroy | |
| 2005/0009159 A1 | 1/2005 | Paterek | |
| 2005/0095690 A1 | 5/2005 | Naik et al. | |
| 2006/0171990 A1 | 8/2006 | Asgari | |
| 2009/0061496 A1 | 3/2009 | Kuhn et al. | |
| 2009/0075354 A1 | 3/2009 | Reneker et al. | |
| 2009/0136932 A1 | 5/2009 | Craighead et al. | |
| 2009/0220378 A1 | 9/2009 | McDonnell et al. | |
| 2009/0221047 A1 | 9/2009 | Schindler et al. | |
| 2009/0258051 A1 | 10/2009 | Chidambaram et al. | |
| 2009/0300745 A1 | 12/2009 | Dispensa | |
| 2009/0305412 A1 | 12/2009 | Ying et al. | |
| 2010/0055154 A1 | 3/2010 | Liao et al. | |
| 2010/0190666 A1 | 7/2010 | Ali et al. | |
| 2011/0165811 A1 | 7/2011 | Hill et al. | |
| 2011/0259804 A1* | 10/2011 | Reitzel | C02F 3/101 210/198.1 |
| 2012/0107900 A1 | 5/2012 | Greiner et al. | |
| 2012/0205041 A1* | 8/2012 | Dalborg | B01D 63/02 156/272.6 |
| 2012/0263771 A1 | 10/2012 | Carlson et al. | |
| 2014/0051144 A1 | 2/2014 | Wackett et al. | |
| 2014/0335148 A1 | 11/2014 | Tong et al. | |
| 2015/0017683 A1* | 1/2015 | Abdullah | C12M 23/24 435/47 |
| 2016/0107912 A1 | 4/2016 | Novak et al. | |

FOREIGN PATENT DOCUMENTS

| | | |
|---|---|---|
| WO | WO-2007/129991 A1 | 11/2007 |
| WO | WO-2008/028194 A2 | 3/2008 |
| WO | WO-2008/075824 A1 | 6/2008 |
| WO | WO-2010/112820 A1 | 10/2010 |
| WO | WO-2011/011468 A2 | 5/2011 |
| WO | WO-2012/064287 A1 | 5/2012 |
| WO | WO-2012/116013 A2 | 8/2012 |
| WO | WO-2012/116013 A3 | 8/2012 |
| WO | WO-2013/070778 A1 | 5/2013 |
| WO | WO-2014/182799 A1 | 11/2014 |

OTHER PUBLICATIONS

"U.S. Appl. No. 14/001,094, Non Final Office Action mailed Dec. 31, 2015", 10 pgs.
"U.S. Appl. No. 14/001,094, Response filed Mar. 24, 2016 to Non Final Office Action mailed Dec. 31, 2015", 15 pgs.
"U.S. Appl. No. 14/001,094, Restriction Requirement mailed Sep. 17, 2015", 6 pgs.
"U.S. Appl. No. 14/271,958, Preliminary Amendment filed Aug. 28, 2014", 3 pgs.
"U.S. Appl. No. 14/271,958, Restriction Requirement mailed Sep. 28, 2015", 6 pgs.
"U.S. Appl. No. PCT/US2014/037128, International Preliminary Report on Patentability mailed Nov. 19, 2015", 9 pgs.
"Canadian Application Serial No. 2,827,559< Voluntary Amendment filed Jun. 18, 2014", 18 pgs.
"Chinese Application Serial No. 201280016435.4, Office Action mailed Jun. 26, 2015", (w/English Translation), 17 pgs.
"European Application Serial No. 12748999.5, Extended European Search Report mailed Apr. 1, 2015", 8 pgs.
"European Application Serial No. 12748999.5, Response filed Oct. 16, 2015 to Extended European Search Report mailed Apr. 1, 2015", 6 pgs.
"International Application Serial No. PCT/US2012/026031, International Preliminary Report on Patentability mailed Mar. 27, 2014", 7 pgs.
"International Application Serial No. PCT/US2012/026031, International Search Report mailed Jun, 6, 2012", 2 pgs.
"International Application Serial No. PCT/US2012/026031, Wrftten Opinion mailed Jun. 6, 2012", 5 pgs.
"International Application Serial No. PCT/US2012/063960, International Preliminary Report on Patentability mailed May 22, 2014", 8 pgs.
"International Application Serial No. PCT/US2012/063960, International Search Report mailed Jan. 23, 2013", 4 pgs.
"International Application Serial No. PCT/U820121063960, Written Opinion mailed Jan. 23, 2013" 8 pgs.
"International Application Serial No. PCT/US2014/037128, International Search Report mailed Aug. 20, 2014", 6 pgs.
"International Application Serial No. PCT/US2014/037128, Written Opinion mailed Aug. 20, 2014", 7 pgs.
"Russian Application Serial No. 2013142684, Office Action mailed Nov. 28, 2013", 4 pgs.
"Russian Federation Application Serial No. 2013142684, Office Action mailed Dec. 4, 2015", (w/ English Translation), 9 pgs.
"Science in Action: Hydraulic Fracturing Research Study", U.S. Environmental Protection Agency (EPA) Office of Research and Development, Document No. EPA/600/F-10/002, (Jun. 2010), 2 pgs.
Brinker, C. J, et al., "Sol-Gel Science: The Physics and Chemistry of Sol-Gel Processing", Chapter 3 Hydrolysis and Condensation II-Silicates, Academic Press, Inc. San Diego, CA, (1990), 99-107.
Dickson, D J, et al., "Photobiological hydrogen production from Synechocystis sp. PCC 6803 encapsulated in silica sol-gel", International Journal of Hydrogen Energy, Elsevier Science Publishers B. V. Banking, GB vol. 34, No. 1, (Jan. 1, 2009), 204-215.
Ferrer, Marla L. et al., "Biocompatible Sol-Gel Route for Encapsulation of Living Bacteria in Organically Modified Silica Matrixes", Chemistry of Materials, 15(19), (2003), 3614-3618.
Fung, W.-Y., et al., "Agrowaste-Based Nanofibers as a Probiotic Encapsulant: Fabrication and Characterization", Journal of Agricultural and Food Chemistry, 59(15), (2011), 8140-8147.
Gensheimer, M., et al., "Novel Biohybrid Materials by Electrospinning: Nanofibers of Poly(ethylene oxide) and Living Bacteria", Advanced Materials, 19, (2007), 2480-2482.
Gensheimer, M., et al., "Polymer/Bacteria Composite Nanofiber Nonwovens by Eledtrospinning of Living Bacteria Protected by Hydrogel Microparticles", Macromoelecular Bioscience, 11(3), (2011), 333-337.
Ho, C, et al., "Enzymatic Properties of Atrazine Chlorohydrolase Entrapped in Biomimetic Silica". Journal of Applied Biological Chemistry, 51(4), (2008), 143-147.
Kandimalla, Vivek B., et al., "Immobilization of Biomolecules in Sol-Gels: Biological and Analytical Applications", Critical Review in Analytical Chemistry, 36(2), (2006), 73-106.

(56) References Cited

OTHER PUBLICATIONS

Kauffmann, C., et al., "Entrapment of atrazine chlorohydrolase in sol-gel glass matrix". Journal of Biotechnology, 62(3), (1998), 169-176.

Kauffmann, C., et al., "Novel Methodology for Enzymatic Removal of Atrazine from Water by CBD-Fusion Protein Immobilized on Cellulose", Environ. Sci. Technol., 34, (2000), 1292-1296.

Kirby, J. R, "Designer bacteria degrades toxin", Nat Chem Biol., 6(6), (Jun. 2010), 398-399.

Klein, S., et al., "Encapsulation of Bacterial Cells in Electrospun Microtubes", Biomacromolecules, 10(7), (2009), 1751-1756.

Klein, S., et al., "Encapsulation of Pseudomonas sp. ADP cells in electrospun microtubes for atrazine bioremediation". Journal of Industrial Microbiology & Biotechnology, 39(11), (2012), 1605-1613.

Liu, Y., et al., "Engineering of bio-hybrid materials by electrospinning polymer-microbe fibers", Proc. Natl. Acad. Sci. USA, 106(34), (2009), 14201-14206.

Lopez-Rubio, A., et al., "Electrospining as a useful technique for the encapsulation of living bifidobacteria in food hydrocolloids", Food Hydrocolloids, 28(1), (2012), 159-167

Lopez-Rubio, A., et al., "Encapsulation of Living Bifidobacteria in Ultrathin PVOH Electrospun Fibers", Biomacromolecules 10, (2009), 2823-2829.

Ma, T., et al., "Enhancement of atrazine degradation by crude and immobilized enzymes in two agricultural soils", Environ Earth Sci., Online Publication, (2011), 7 pgs.

Ma, Y., et al., "The Research of Immobilized Atrazine Degrading Bacteria Degrading Characteristics", International Conference on Environmental Science and Information Application Technology, 2009. ESIAT 2009, vol. 1, (2009), 677-680.

Macias-Flores, A., et al., "Atrazine biodegradation by a bacterial community immobilized in two types of packed-bed biofilm reactors", World J Microbiol Biotechnol., 25, (2009), 2195-2204.

Mantsch. H. H, et al., "Infrared Spectroscopy of Biomolecules", Chapter 9, Section 9.7.2.1, Wily-Liss, Inc., New York, (196), p. 266.

Meunier, C F, et al., "Encapsulation of cells within silica matrixes: Towards a new advance in the conception of living hybrid materials", Journal of Colloid and Interface Science, Acadamic Press, New York, NY US, vol. 342, No. 2, (Feb. 15, 2010), 211-224.

Meunier, Christophe F., et al., "Investigation of different silica precursors: Design of biocompatible silica gels with long term bio-activity of entrapped thylakoids toward artificial leaf", Journal of Materials Chemistry, 19, (2009), 4131-4137.

Mutlu, Baris R., et al., "Silicon alkoxide cross-linked silica nanoparticle gels for encapsulation of bacterial biocatalysts", Journal of Materials Chemistry A, (2013), 10 pgs.

Nedovic, V., et al., *Fundamentals of Cell Immobilization Biotechnology*. adapted from p. 15, Part 1, (2003), 36 pgs.

Patel, Alpa C, et al., "In Situ Encapsulation of Horseradish Peroxidase in Electrospun Porous Silica Fibers for Potential Biosensor Applications", Nano Letters, vol. 6, No. 5, (May 1, 2006), 1042-1046.

Reategui, E., et al., "Encapsulation of Mammalian Cells in Hybrid Inorganic Matrices for Developing Bio-detection Applications", Alley Conference 2010, Poster, (2010), 1 pg.

Reategui, E., et al., "Silica gel-encapsulated AtzA biocatalyst for atrazine biodegradation", Appl Microbiol Biotechnol., [Epub ahead of print], (Jan. 7, 2012), 10 pgs.

Reetz, Manfred T., "Chapter 6—Practical Protocols for Lipase Immobilization", *Immobilization of Enzymes and Cells*. Second Edition—Edited by Jose M. Guisan, (2006), 65-76.

Riddle, Kathryn W, et al., "Biomaterials for Cell Immobilization: A look at carrier design", Kathryn W. Riddle and David J. Mooney, University of Michigan, Chemical Engineering, (2004), 19 pgs.

Rietti-Shati, M, et al., "Atrazine Degradation by Pseudomonas strain ADP Entrapped in Sol-Gel Glass", Journal of Sol-Gel Science and Technology, v.7, No. 1-2, (1996), 77-79 pgs.

Rim, N. G., et al., "Current approaches to electrospun nanofibers for tissue engineering", Biomedical Materials, 8(1), (2013), 1-14.

Ruiz-Hitzky, Eduardo, et al., "An Introduction to Bio-nanohybrid Materials", Bio-inorganic Hybrid Nanomaterials, Edited by Eduardo Ruiz-Hitzky, Katsuhiko Ariga and Yuri Lvov, (2008), 1.

Salalha, W., et al., "Encapsulation of bacteria and viruses in electrospun nanofibres", Nanotechnology, 17, (2006), 4675-4681.

Shona, Pek Y, et al., "A thixotropic nanocomposite gel for three-dimensional cell culture", Nature Nanotechnology vol. 3, No. 11, (Sep. 28, 2008), 671-675.

Siripattanakul, S., et al., "Atrazine removal in agricultural infiltrate by bioaugmented polyvinyl alcohol immobilized and free Agrobacterium radiobacter J14a: A sand colomn study", Chemosphere, 74, (2009), 308-313.

Srivastava, Y., et al., "Electrospinning of hollow and core/sheath nanofibers using a microfluidic manifold". Microfluidics and Nanofluidics, 4(3), (2007), 245-250.

Tafoya-Garnica, A., et al., "Kinetics of atrazine biodegradation by suspended and immobilized mixed microbial cells cultivated in continuous systems", Journal of Chemical Technology & Biotechnology, 84(7), (Jul. 2009), 982-991.

Vivek, Kandimalla, et al., "Immobilization of Biomolecules in Sol-Gels Biological and Analytical Applications", Critical Reiviews in Analytical Chemistry, vol. 36, No. 2, (Jul. 1, 2006), 73-106.

Wright, J. D. "Sol-Gel Materials: Chemistry and Applications", Chapter 2: Silica Sol-Gels: Reaction Mechanisms, Gordon and Breach Science Publishers, (2001), 15-31.

Yu, M., et al., "RNA sequencing of pancreatic circulating tumour cells implicates WNT signalling in metastasis". Nature, 487(7408), (2012), 510-515.

Zhang, X., et al., "Flexible Generation of Gradient Electrospinning Nanofibers Using a Microfluidic Assisted Approach", Langmuir, 28(26), (2012), 10026-10032.

Zou, et al., "Polymer/Silica Nanocomposites: Preparation, Characterization, Properties, and Application", Chem. Rev, (2008), 3893-3957.

Zussman, E,, "Encapsulation of cells within electrospun fibers", Polymers for Advanced Technologies, 22(3), (2011), 366-371.

\* cited by examiner

MEMBRANES FOR WASTEWATER-GENERATED ENERGY AND GAS

CLAIM OF PRIORITY

This application claims the benefit of priority of U.S. Provisional Patent Application Ser. No. 61/774,857, filed on Mar. 8, 2013, which is herein incorporated by reference in its entirety.

GOVERNMENT FUNDING

This invention was made with government support under Award Number DMR-0819885 awarded by the National Science Foundation through the University of Minnesota MRSEC. The United States Government has certain rights in the invention

BACKGROUND

Wastewater or sewage treatment is an important process used to remove physical, chemical, or biological contaminants. Typically, an objective of wastewater treatment is to produce an environmentally safe fluid waste stream or a solid waste suitable for disposal or further use. Wastewater treatment methods typically involve multiple steps including, but not limited to, pretreatment, primary treatment, aeration, secondary treatment, and sludge treatment. The multiple processes involved in wastewater treatment can consume a large amount of energy.

SUMMARY

Certain embodiments disclosed herein use a polymer membrane containing bacteria to extract energy from wastewater. Embodiments can include a membrane including one or more hollow fibers, wherein the hollow fibers can be configured to convey a gas produced during treatment of a wastewater fluid. Bacteria can be immobilized within the membrane, wherein the bacteria can produce the gas during treatment of the wastewater. Embodiments provide increased gas or energy recovery from current wastewater treatment techniques. For example, by immobilizing the bacteria in the membrane, concentrations of bacteria can be optimized to produce a desired amount of gas, such as hydrogen. Further, because the bacteria are immobilized, they are protected from harmful influences and can be permitted to grow within the membrane.

Embodiments can provide extraction of various gasses during degradation of organic contaminants in a wastewater stream. For example, hydrogen, carbon dioxide, or methane can be extracted and further used either industrially (e.g., carbon dioxide) or to produce useful, clean energy (e.g., hydrogen or methane). Embodiments of the present disclosure provide the use of various types of bacteria, including, but not limited to, acetogenic and methanogenic bacteria. Advantages of such embodiments include extracting clean, non-greenhouse gases, such as hydrogen.

Various embodiments can include a composite membrane used in various stages of a typical wastewater treatment system. In an embodiment, the membrane can be placed in a recycle stream of a wastewater treatment system. Recycle streams typically have an increased concentration of organic contaminants, such that the increased levels of contaminants can provide a driving force for the bacteria to produce a useful gas. Further embodiments include, placing the membrane in a wastewater treatment facility prior to an aeration step, commonly used in facilities today. Such embodiments can provide the benefit of reducing an amount of energy necessary to aerate the wastewater fluid. For example, the bacteria immobilized within the membrane partially break down the organic compounds to produce a useful gas for extraction. Because the energy necessary to aerate a wastewater stream depends on the type and concentration of organic compounds present, the partially broken down compounds can be aerated with expending less energy than complete or non-broken down organic compounds.

BRIEF DESCRIPTION OF THE DRAWINGS

In the drawings, which are not necessarily drawn to scale, illustrate generally, by way of example, but not by way of limitation, various embodiments discussed in the present document.

DETAILED DESCRIPTION

Wastewater, including any water that has been affected by an anthropogenic influence, such as, human waste, washing water, rainfall, industrial waste, highway drainage, among others, is a potential source of energy. However, treating wastewater consumes a substantial amount of energy to reuse or reintroduce the water to the environment. Wastewater contaminants, as described herein, typically are nutrient and energy dense compounds. The present inventors recognize that energy can be extracted from these energy dense compounds. According to the present disclosure, a composite fermentative membrane can be used to extract gas, usable as a source of energy or an industrial product, from wastewater contaminants. The composite fermentative membrane of the present disclosure can use wastewater as an input to generate a clean-burning product, such as hydrogen or methane, or an industrial product, such as carbon dioxide, with less post-processing than current wastewater methods and systems. Embodiments according to the present disclosure include membranes, systems, and associated methods for extracting or producing a gas from wastewater stream.

Figure 1:
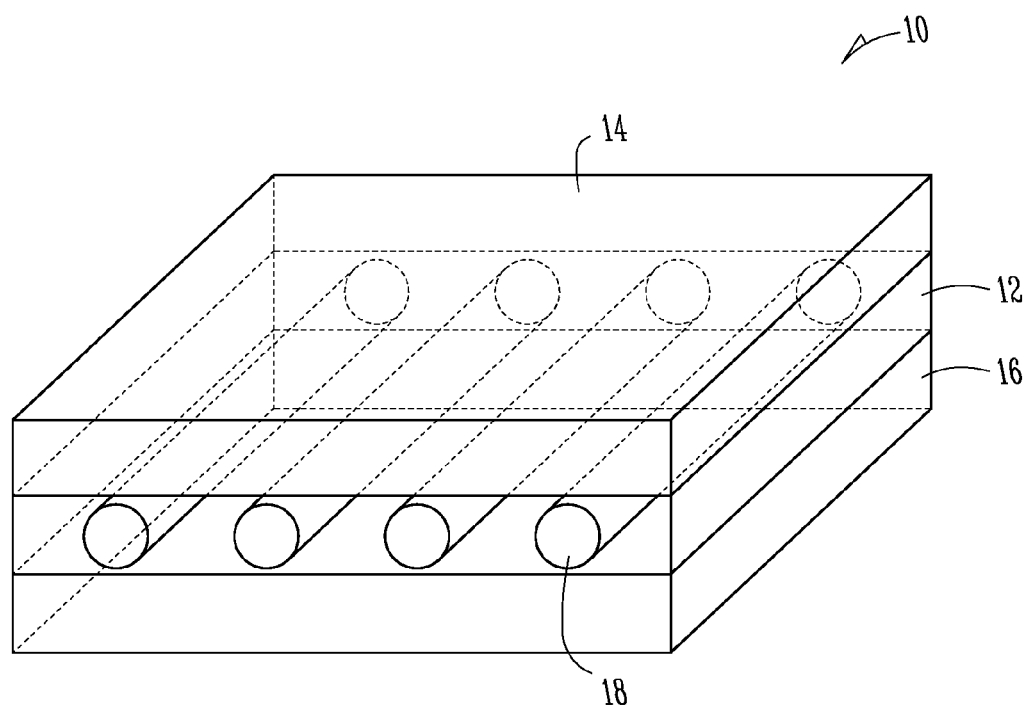
FIG. 1 is a perspective view of a section of a composite membrane, according to an embodiment.

FIG. 1 illustrates an example of a composite membrane 10, according to the present disclosure. In various embodiments, the composite membrane 10 immobilizes bacteria and facilitates gas collection, so as to provide increased gas production from waste, such as organic compounds in wastewater, and reliable scale-up. Although production of various types of gases is contemplated, the present disclosure generally refers to production of hydrogen. The bacteria are immobilized in a first layer 12. This first layer 12 is disposed between a second layer 14 and a third layer 16. The composite membrane 10 is generally referred to as a sandwich structure as the bacteria are immobilized in a first layer 12 sandwiched between the second layer 14 and the third layer 16. In various embodiments, the first layer 12 includes a polymer, a copolymer, a block copolymer matrix, or combinations thereof, including, but not limited to poly (vinyl alcohol), polyacrylamide, poly(ethylene oxide), polypropylene oxide, latex, nylon, Pluronic F127 dimethacrylate, or combinations thereof. The polymer, copolymer, or block copolymer contains an immobilized bacteria, such as acetogenic bacteria or methanogenic bacteria. Such a design, for example, facilitates the use of pure cultures of acetogens, chosen for their hydrogen producing capabilities, as well as engineered hydrogen-producing communities or genetically engineered organisms capable of hydrogen production.

To collect a gas, such as hydrogen, carbon dioxide, methane, or combinations thereof, as it is produced by the reactions between the immobilized bacteria and the wastewater, at least one hollow fiber 18 is embedded within the first layer 12. Embedding the hollow fiber 18 within the polymer matrix containing acetogens, allows for efficient hydrogen collection, so as to increase hydrogen production and overall hydrogen yield. Finally, a modular design, such as a composite membrane rack fitted with a gas collection manifold, can enable use of the system at any scale. Further purification and concentration of the hydrogen can be accomplished with typical systems commercially available.

In various embodiments, the second layer 14 and third layer 16 includes a polymer, a copolymer, a block copolymer matrix, or combinations thereof, including, but not limited to poly(vinyl alcohol), polyacrylamide, poly(ethylene oxide), polypropylene oxide, latex, nylon, Pluronic F127 dimethacrylate, or combinations thereof. In an example, the second layer 14 is the same material or a different material as the first layer 12. In an example, the third layer 16 is the same material or is a different material as the first layer 12. Further, the second layer 14 and third layer 16, in an example, are the same material or are a different material. In an example, the second layer 14 and third layer 16 do not contain immobilized bacteria.

In an example, the immobilized material includes acetogenic bacteria, which produce hydrogen via the fermentation of carbohydrates, organic acids, and alcohols. In anaerobic environments, however, hydrogen generated by acetogenic bacteria is quickly consumed by methanogenic bacteria, producing methane. It is the consumption of the hydrogen that allows acetogenesis to occur, as this hydrogen-producing reaction is not thermodynamically favorable at high hydrogen partial pressures. Enriched or isolated acetogenic bacteria in combination with efficiently removing hydrogen, permits these organisms to be used to generate hydrogen from the fermentable compounds found in wastewater. The biochemically-derived hydrogen from wastewater is a "free" substrate and the fermentation is anaerobic, resulting in no real cost for biohydrogen production other than the capture of the product. In various examples, the immobilized bacteria include methanogenic bacteria.

Figure 2:
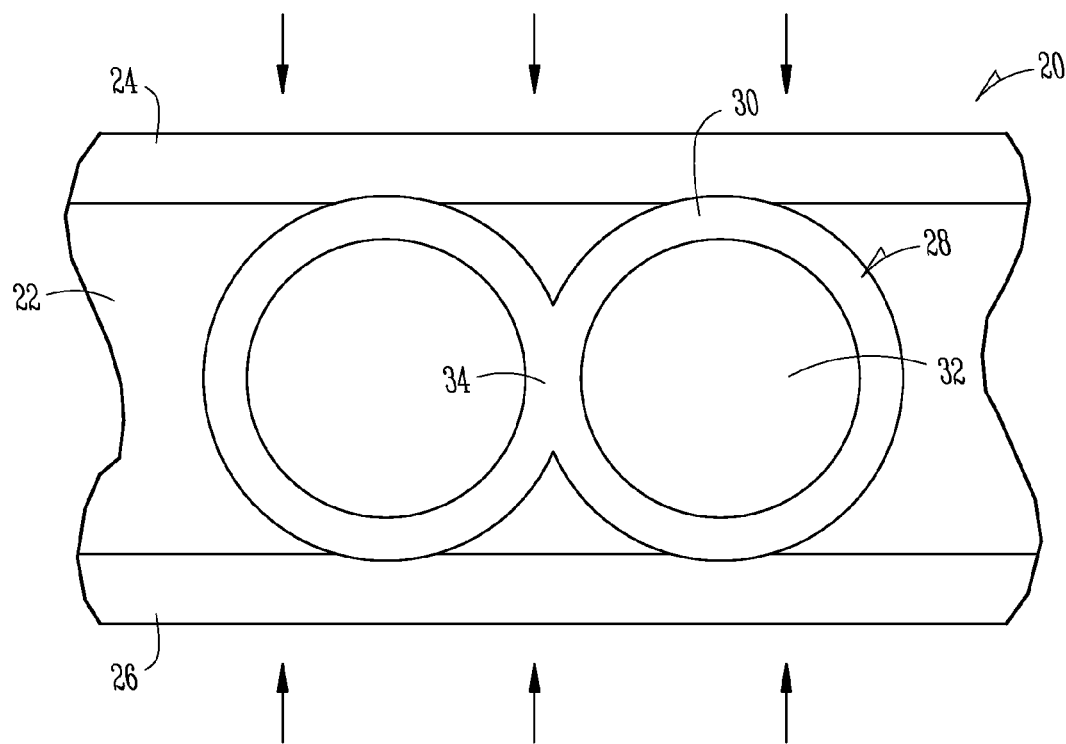
FIG. 2 is a view of a membrane, according to an embodiment.

In an example, free and immobilized cells of *C. butyricum* are used for their ability to generate hydrogen via the fermentation of hexoses, including glucose. Municipal wastewater, however, is a complex mixture of compounds, including organic acids. *Clostridium kluyveri* is capable of fermenting acetate and alcohols; as such, it is capable of using additional components of the waste stream for hydrogen production. Hydrogen production from the synthetic wastewater feed by immobilized *C. butyricum, C. kluyveri*, and a mixture of the two organisms in the composite fermentative membrane modules are contemplated. Immobilization of other combinations of hydrogen-, methane-, and carbon dioxide-producing bacteria are also contemplated.

The composite membrane 10 uses the diffusive transport of carbon and energy sources to the immobilized acetogenic bacteria and the diffusive transport of hydrogen away from the cell surface and into the hollow-fiber membrane. A combination of reaction-diffusion equations (Equation 1 below), paired with hydrogen production rates, r, is used to describe concentration profiles, C, of substrate and hydrogen in the composite fermentative membrane as a function of depth, x, and time, t.

$$\frac{\partial C}{\partial t} = \frac{\partial^2 C}{\partial x^2} \pm r \quad (1)$$

In an example, the composite membrane 10 is designed to control chemical diffusion and to maintain pure culture viability and activity. Further, as described herein, membrane behavior can be understood mathematically, so as to effectively model the transport of reactants and products through the membranes to predict and optimize performance.

Polyacrylamide has been shown to immobilize bacteria, such as *Burkholderia xenovorans* strain LB400, and preserve their activity for at least 10 months; *Burkholderia xenovorans* strain LB400 is an aerobic PCB-degrading bacterium. Other types of bacteria, such as methanogens or acetogens, can be immobilized in the polymer, as described herein. A benefit of the polymer matrix, as described in the present disclosure, includes providing diffusion limitations that can be used to promote the capture of the hydrogen produced therein. Dissolution and diffusion of wastewater compounds in the dense polyacrylamide structure provides a constant stream of carbon and nutrients for consumption by the immobilized bacteria. Other polymers, for example, a polymer, copolymer, and/or block copolymer matricies, including, but not limited to poly(vinyl alcohol), polyacrylamide, poly(ethylene oxide), polypropylene oxide, latex, nylon, Pluronic F127 dimethacrylate, or combinations thereof, are used to immobilize the bacteria and preserve their activity, in various examples.

The hollow fibers 18 are in close contact with the acetogens that produce the hydrogen, consequently substantially enhancing the efficiency of hydrogen collection. Different types of hollow fiber membranes can be used, each with respective efficiency in collecting hydrogen from the fermentative membrane. Two examples of hollow fiber membranes include: non-porous silicone and microporous polyethylene. Silicone membranes have the benefit that they are durable and robust. Porous polyethylene membranes have the potential to draw hydrogen away from cell surfaces more quickly than silicone due to fast mass transport through their pores. Combinations of no-porous silicone and microporous polyethylene hollow fibers are contemplated.

Hydrogen production and collection efficiencies can be optimized through manipulation of the composite fermentative membrane module configuration. FIG. 2 illustrates a view of a composite membrane 20, according to an embodiment. The composite membrane 20 includes a first layer 22 of a polymer including immobilized bacteria, as described herein. The first layer 22 is disposed between a second layer 24 and a third layer 26, as described herein. FIG. 2 illustrates hollow fibers 28 which are embedded at least partially in the first layer 22, the second layer 24, and the third layer 26. The hollow fibers 28 include a hollow fiber membrane wall 30. In various examples, a thickness of the hollow fiber membrane wall 30 is varied so as to increase efficiency of the gas diffusing into a lumen 32 or increase quality of the gas collected. For example, thickness of the hollow fiber membrane wall 30 is thinner at the first layer 22, relative to the thickness of the hollow fiber membrane wall 30 thickness at the second layer 24 and the third layer 24. Such an example provides the benefit of allowing easier diffusion of the gas from the first layer 22, into the lumen 32. In an example, the hollow fiber membrane wall 30 has a uniform thickness. Further, an intersection 34 of the two hollow fibers 28 of FIG. 2 includes an overlap of the two hollow fibers 28, such that the hollow fiber construction of the composite membrane is more rigid. That is, the intersection 34 has a greater thickness than the thickness of an individual hollow fiber membrane wall 30.

Sandwiched or layered configurations, such as composite membrane 20 control transport into and out of a reactive layer, such as the first layer 22. Likewise, acetogen-embedded polyacrylamide layers (e.g., first layer 22) can be separated from the wastewater with a thin layer of organism-free polyacrylamide, such as the second layer 24 and the third layer 26, to further isolate a zone of hydrogen production from the free solution in the reactor. For example, the arrows indicate where the wastewater contacts the composite membrane 20. A sandwich configuration can increase the area of influence of the hollow fibers 28, improving gas collection and reducing diffusion toward the solution where it would be lost. Many variations on sandwich or layered configurations are contemplated to maximize gas production and capture.

Figure 3:
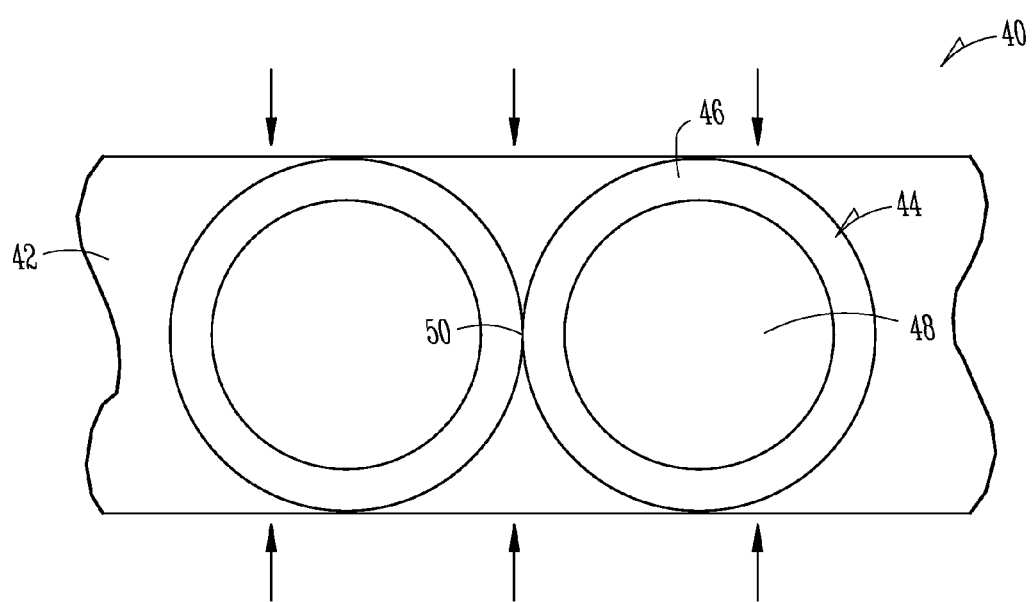
FIG. 3 is a view of an alternative membrane, according to an embodiment.

FIG. 3 illustrates an example of a view of a composite membrane 40. The composite membrane 40 includes a first layer 42 of a polymer including immobilized bacteria, as described herein. The composite membrane 40 does not include a second layer or a third layer, as described in reference to FIG. 1 and FIG. 2. As such, the wastewater, as indicated by the arrows, contacts the first layer 42. Further, the hollow fibers 44 are located proximate one another, so as to form an alternative intersection 50. The intersection 50 is defined by a contact point of the hollow fiber membrane wall 46 of each of the hollow fibers 44. The hollow fiber membrane walls 46 have a varying thickness or a constant thickness, so as to promote gas collection or composite membrane rigidity. The lumen 48 can have any cross-section geometry, such as circular, elliptical, triangular, square, rectangular, or the like.

Figure 4:
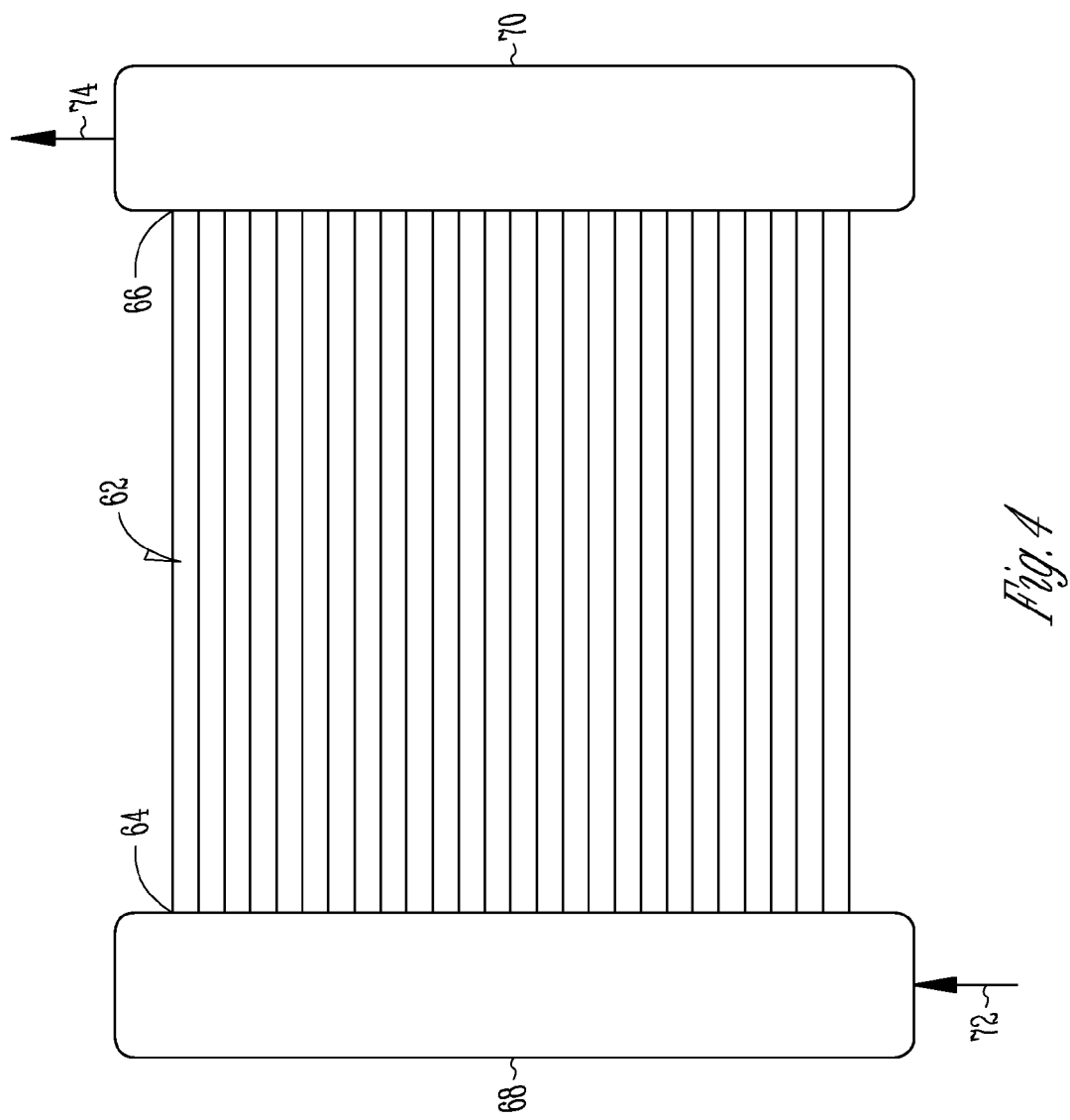
FIG. 4 is an diagram of a membrane system, according to an embodiment.

FIG. 4 illustrates a diagram of a potted membrane system 60, according to an example. Open ends 64, 66 of the hollow fibers 62 are potted (e.g., affixed) into a gas flow-through system. Potted includes at least one of a compression fitting, such as a snap fit or press fit, adhering, such as with an adhesive or a sealant, and any other technique used to connect the hollow fibers 62 with the first and second manifold 68, 72. For example, the first open end 64 of the hollow fibers 62 is potted to a first manifold 68. The second open end 66 is potted to a second manifold 70. The hollow fibers 62 are in fluid communication with the first and second manifolds 68, 72, such that gas can flow from the first manifold 68, through the hollow fibers 62, and to the second manifold 70. That is, an inert gas, such as nitrogen, is provided 72 to the first manifold, so as to flush the hollow fibers 62, including any collected gas, and is pushed through the second manifold 70, towards further production 74. In an example, the produced gas is vacuumed from the hollow fibers 62, such as through the second manifold 70.

Close spacing of the hollow fibers 62 improves the ability of the system 60 to draw hydrogen from cell surfaces with higher gas flow or vacuum rates to remove the hydrogen from the hollow fibers 62. To optimize fiber spacing, hollow-fiber fabrics can be used as-is and with alternate fibers removed to alter hydrogen production and use fewer collection locations.

Figure 5:
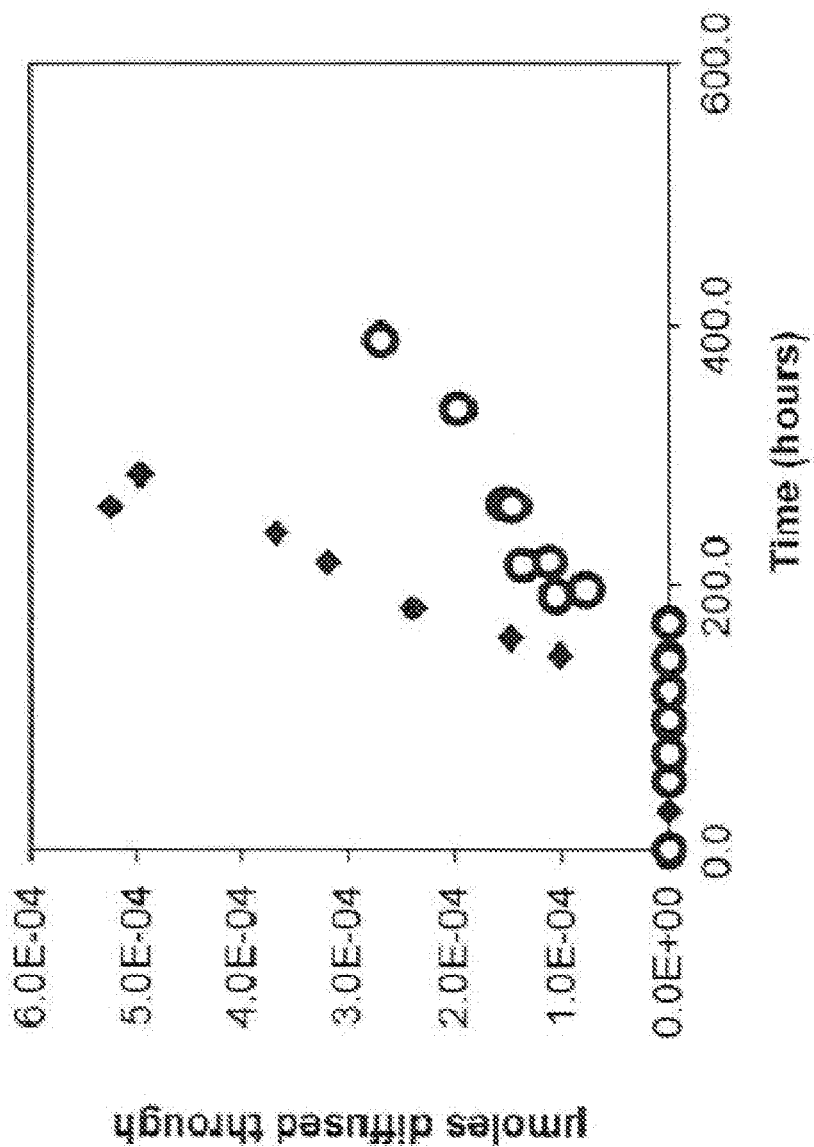
FIG. 5 is a plot of a breakthrough curve for 2,3',4',5-chlorobiphenyl diffusing through polyacrylamide, according to an embodiment.

FIG. 5 is a plot 80 of a breakthrough curve for 2,3',4',5-chlorobiphenyl diffusing through polyacrylamide, according to an embodiment. The plot 80 indicates that composite membranes containing bacteria capable of degrading 2,3',4',5-chlorobiphenyl increase the time to 2,3',4',5-chlorobiphenyl breakthrough and its subsequent flux through the composite membrane. Such information is used to model or configure membrane thicknesses, such as during casting or extrusion to provide that the diffusion from the cell surface toward a hollow fiber (18, FIG. 1) is preferred over diffusion toward the solution in the reactor and to optimize the quantity of bacteria immobilized in the polymer. Polyacrylamide is an example of a hydrophilic polymer that used for the immobilization of the bacteria.

Figure 6:
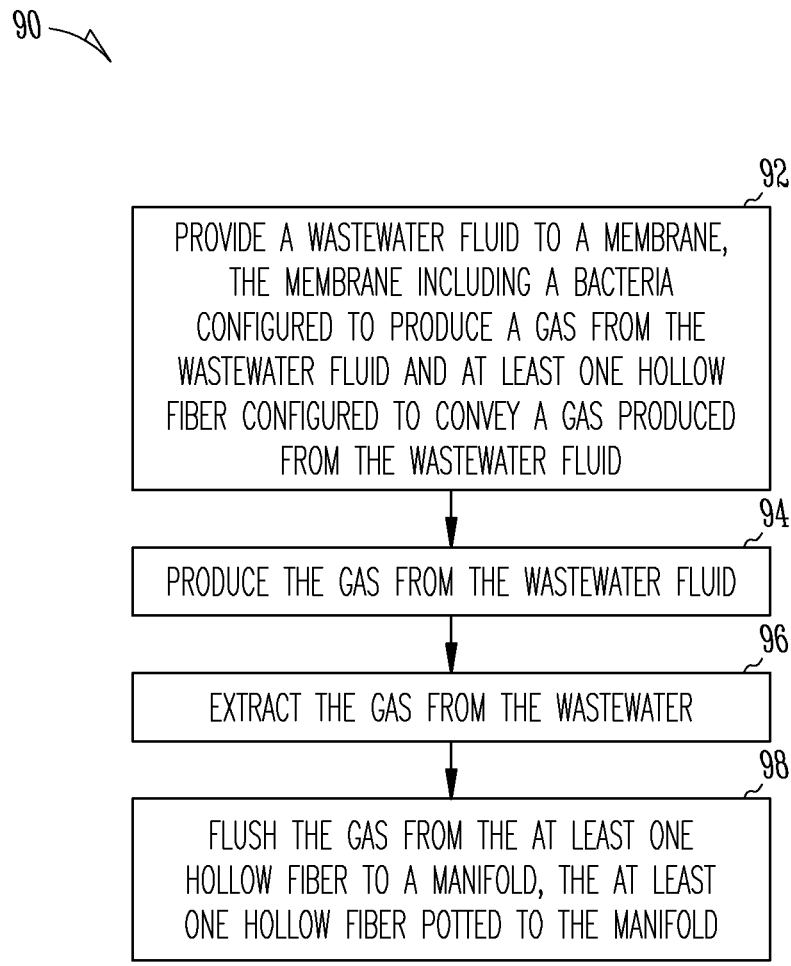
FIG. 6 is a method for producing and extracting a gas from a wastewater, according to an embodiment.

FIG. 6 is a method 90 for producing and extracting a gas from a wastewater, according to an embodiment. At 92, the method 90 includes providing a wastewater fluid to a membrane, such as composite membrane system 60 of FIG. 4. In an example, the membrane is immersed in the wastewater. In an example, the system is configured to operate in batch mode, so as to treat discrete amounts of water. Additionally, in an example, the system is configured to operate in a continuous or flow through mode. In the flow through mode, a residence time or membrane area is altered to maximize treated water quality or gas production. The residence time is altered by adjusting the reactor volume or adjusting a flow rate of the waste water through or around the membrane. The membrane includes a bacteria immobilized within the membrane, the bacteria configured to produce a gas from a wastewater fluid, as described herein. Further, the membrane includes at least one hollow fiber configured to convey the gas produced from the wastewater fluid, such as within a lumen, as described herein.

At 94, the gas is produced from at least one of acetogenesis and methanogenesis, as described herein. At, 96, the produced gas is extracted from the wastewater. For example, the gas diffuses through a hollow fiber membrane wall of the at least hollow fiber, as described herein.

At 96, the method 90 includes flushing the gas from the at least one hollow fiber to a manifold, wherein the at least one hollow fiber is potted to the manifold. In an example, the at least one hollow fiber is flushed with an inert gas, such as nitrogen. The inert gas is pumped from a first end of the at least one hollow fiber (64, FIG. 4) to a second end (66, FIG. 4). The second end of the at least one hollow fiber is potted to a second manifold (70, FIG. 4) which provides the inert gas and produced gas for further processing, such as purification.

Experiment

Figure 7:
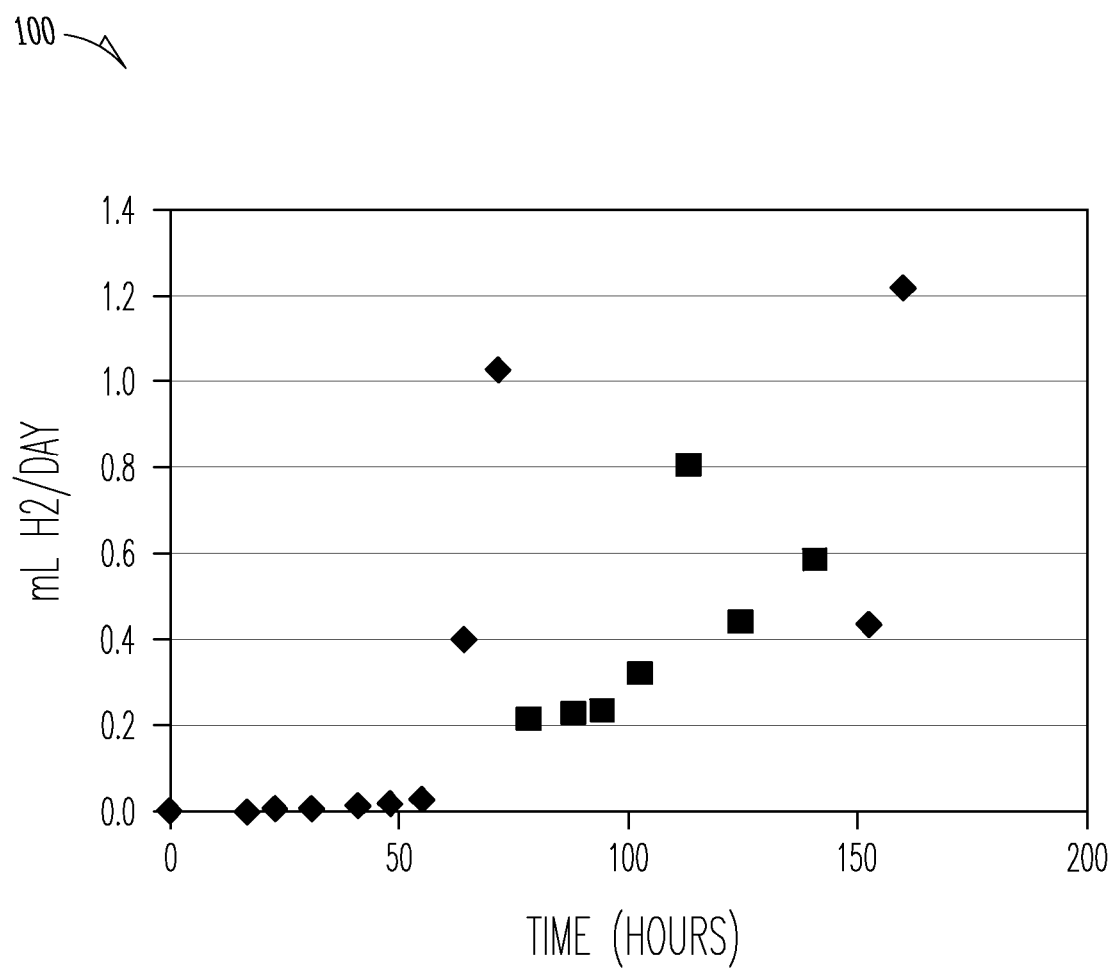
FIG. 7 is a plot of hydrogen measurements taken from alternative hollow fiber constructions.

The hollow fiber membrane was tested in a non-sterilized completely stirred tank reactor that was continuously fed for approximately 7 days. The reactor was fed a specialized glucose-based bacterial media for *Clostridium*. The hollow fibers were plumbed into a plastic manifold used to supply a continuous flow of nitrogen gas through the hollow fibers. As seen in FIG. 7, the plot 100 indicates that after approximately 24 hours hydrogen was detected in the exit nitrogen stream via gas chromatography. The diamond data points of FIG. 7 represent measurements taken with electrospun fibers containing *C. butyricum* woven onto hollow fibers installed in the reactor. The square data points of FIG. 7 represent measurements taken with bare hollow fibers installed in the reactor.

Hydrogen capture rose to a rate of 1 mL/day before the membrane module was swapped for a negative control that consisted of bare hollow fibers. Hydrogen capture rates dropped to an average of 0.5 mL/day, indicating that hydrogen production was occurring in the bulk media solution. After 140 hours, the membrane modules were swapped once again, with the same electrospun membrane containing *C. butyricum* reinstalled. Hydrogen rates briefly rose to 1.2 mL/day before the run was aborted due to a leak in the membrane module. Higher hydrogen production rates when the biologically active membrane was installed may suggest a concentration gradient of hydrogen gas created by the immobilized bacteria close to the hollow fiber surfaces resulted in higher capture rates.

While the pure culture *C. butyricum* was capable of producing hydrogen from a glucose solution, they were not able to produce hydrogen from synthetic wastewater. A second mixed microbial culture was therefore enriched from an anaerobic wastewater seed that was able to produce hydrogen from synthetic wastewater. Using small batch reactors, it was demonstrated that these bacteria can be successfully embedded in a polyvinyl alcohol (PVA) membrane and fed synthetic wastewater to produce hydrogen gas.

Various Notes and Examples

Example 1 can include subject matter such as an apparatus for producing and extracting a gas from a wastewater fluid, comprising: a membrane including immobilized bacteria, wherein the immobilized bacteria is configured to produce a gas from one or more compounds in a wastewater fluid; and at least one hollow fiber within the membrane, the at least one hollow fiber configured to convey the gas produced by the immobilized bacteria.

Example 2 can include, or can optionally be combined with the subject matter of Example 1, to optionally include wherein the gas is at least one of hydrogen, carbon dioxide, and methane.

Example 3, can include, or can optionally be combined with the subject matter of one or any combination of Examples 1 or 2, to optionally include wherein the immobilized bacteria is at least one of acetogenic bacteria and methanogenic bacteria.

Example 4 can include, or can optionally be combined with the subject matter of one or any combination of Examples 1-3, to optionally include wherein the membrane includes at least one layer of a first polymer, wherein the immobilized bacteria is immobilized in at least a portion of the at least one layer of the first polymer.

Example 5 can include, or can optionally be combined with the subject matter of one or any combination of Examples 1-4, to optionally include wherein at least one of the at least one layer of the first polymer is disposed between at least one layer of a second polymer.

Example 6 can include, or can optionally be combined with the subject matter of one or any combination of Examples 1-5, to optionally include wherein the hollow fibers are configured to draw the gas produced by the immobilized bacteria from the first polymer into the hollow fibers.

Example 7 can include, or can optionally be combined with the subject matter of one or any combination of Examples 1-6, to optionally include wherein the first polymer or the second polymer is at least one of poly(vinyl alcohol), polyacrylamide, and poly(ethylene oxide), polypropylene oxide, latex, nylon, and Pluronic F127 dimethacrylate.

Example 8 can include, or can optionally be combined with the subject matter of one or any combination of Examples 1-7, to optionally include wherein the second polymer is substantially abiotic.

Example 9 can include, or can optionally be combined with the subject matter of one or any combination of Examples 1-8, to optionally include wherein the second polymer and the first polymer are substantially the same.

Example 10 can include, or can optionally be combined with the subject matter of one or any combination of Examples 1-9, to optionally include wherein the second polymer is configured to substantially prevent diffusion of the extracted gas into the second polymer.

Example 11 can include, or can optionally be combined with the subject matter of one or any combination of Examples 1-10, to optionally include wherein the at least one hollow fiber includes a fiber material, the fiber material including at least one of silicone, polypropylene, and polyethylene.

Example 12 can include, or can optionally be combined with the subject matter of one or any combination of Examples 1-11, to optionally include wherein the membrane has a thickness of about 0.2 millimeters to about 1.0 centimeters.

Example 13 can include, or can optionally be combined with the subject matter of one or any combination of Examples 1-12, to optionally include wherein the at least one hollow fiber comprises a hydrophobic or hydrophilic material.

Example 14 can include, or can optionally be combined with the subject matter of one or any combination of Examples 1-13, to optionally include wherein the at least one hollow fiber is potted at a first end to a first manifold and potted at a second end to a second manifold, wherein the at least one hollow fiber is configured to convey the gas to the second manifold.

Example 15 can include subject matter such as a method for producing and extracting a gas from a wastewater, comprising: providing a wastewater fluid to a membrane, the membrane including, a bacteria immobilized within the membrane, the bacteria configured to produce a gas from a wastewater fluid; and at least one hollow fiber, the at least one hollow fiber configured to convey the gas produced from the wastewater fluid; producing the gas from the wastewater fluid; extracting the gas from the wastewater; and flushing the gas from the at least one hollow fiber to a manifold in which the at least one hollow fiber is potted.

Example 16 can include, or can optionally be combined with the subject matter of Example 15, to optionally include wherein producing the gas comprises at least one of acetogenesis and methanogenesis.

Example 17 can include, or can optionally be combined with the subject matter of one or any combination of Examples 15 or 16, to optionally include wherein flushing the gas comprises vacuuming the gas from the at least one hollow fiber through the manifold.

Example 18 can include, or can optionally be combined with the subject matter of one or any combination of Examples 15-17, to optionally include wherein flushing the gas comprises pumping an inert gas through the at least one hollow tube.

Example 19 can include, or can optionally be combined with the subject matter of one or any combination of Examples 15-18, to optionally include drawing the gas away from the bacteria and into the at least one hollow fiber.

Example 20 can include subject matter such as a system, comprising: a membrane including a plurality of hollow fibers, each of the plurality of hollow fibers potted at a first end of each of the plurality of hollow fibers to a first manifold and potted at a second end of each of the plurality of hollow fibers to a second manifold, wherein the membrane is configured to convey a gas produced from and extracted from a wastewater stream to the second manifold; a bacteria immobilized within a first polymer of the membrane, the bacteria configured to produce the gas from the wastewater fluid, the plurality of hollow fibers in contact with the first polymer and the plurality of hollow fibers configured to draw the gas from the first polymer into the plurality hollow fibers; and at least one layer of a second polymer, wherein the first polymer is adjacent to at least one layer of the second polymer, wherein the second polymer is configured to substantially prevent diffusion of the extracted gas out of the apparatus.

Example 21 can include the subject matter, including the apparatus, system, and method, of one or any combination of Examples 1-20.

Each of these non-limiting examples can stand on its own, or can be combined in any permutation or combination with any one or more of the other examples.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Although the invention has been described with reference to specific example embodiments, it will be evident that various modifications and changes can be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural and logical substitutions and changes can be made without departing from the scope of this invention. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This invention is intended to cover any and all adaptations or variations of various embodiments. Combinations of the above embodiments, and other embodiments not specifically described herein, will be apparent to those of skill in the art upon reviewing the above description.

The Abstract of the Invention is provided to comply with 37 C.F.R. §1.72(b), requiring an abstract that will allow the reader to quickly ascertain the nature of the technical invention. It is submitted with the understanding that it will not be used to interpret or limit the scope or meaning of the claims. In addition, in the foregoing Detailed Description, it can be seen that various features are grouped together in a single embodiment for the purpose of streamlining the invention. This method of invention is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus for producing a hydrogen gas from a wastewater fluid, comprising:
    a membrane including:
        a first layer of a first polymer;
        immobilized acetogenic bacteria, wherein the immobilized acetogenic bacteria are immobilized within the first polymer and configured to produce a hydrogen gas in a hydrogen production zone from one or more compounds in a wastewater fluid,
        a second layer of a second polymer, the second layer adjacent the first layer;
        a third layer of a third polymer, the third layer adjacent the first layer, the second layer and the third layer being substantially abiotic, the second layer and the third layer configured to isolate the hydrogen production zone from the wastewater fluid; and
    a plurality of hollow fibers embedded within the first layer, the plurality of hollow fibers configured to convey the hydrogen gas produced by the immobilized acetogenic bacteria away from the membrane.

2. The apparatus of claim 1, wherein the hollow fibers are configured to permit passage of the gas produced by the immobilized bacteria from the first polymer into the hollow fibers.

3. The apparatus of claim 1, wherein the first polymer, the second polymer, and the third polymer include at least one of poly(vinyl alcohol), polyacrylamide, and poly(ethylene oxide), polypropylene oxide, latex, nylon, and Pluronic F127 dimethacrylate.

4. The apparatus of claim 1, wherein the first polymer, the second polymer, and the third polymer are substantially the same.

5. The apparatus of claim 1, wherein the first polymer is configured to substantially prevent diffusion of the produced gas into the second polymer and the third polymer.

6. The apparatus of claim 1, wherein the plurality of hollow fibers includes a fiber material the fiber material including at least one of silicone, polypropylene, and polyethylene.

7. The apparatus of claim 1, wherein the membrane has a thickness of about 0.2 millimeters to about 1.0 centimeters.

8. The apparatus of claim 1, wherein the plurality of hollow fibers are formed of a hydrophobic material or a hydrophilic material.

9. The apparatus of claim 1, wherein the plurality of hollow fibers are potted at a first end to a first manifold and potted at a second end to a second manifold, wherein the plurality of hollow fibers are configured to convey the gas to the second manifold.

10. A system, comprising:
 a membrane including a plurality of hollow fibers each having a first end and a second end, the first end potted to a first manifold, the second end potted to a second manifold, wherein the membrane is configured to convey a hydrogen gas produced from and extracted from a wastewater stream to the second manifold;

an acetogenic bacteria immobilized within a first polymer layer of the membrane, the acetogenic bacteria configured to produce the gas from the wastewater fluid in a hydrogen production zone, the plurality of hollow fibers embedded within the first polymer layer and the plurality of hollow fibers configured to draw the gas from the first polymer layer into the plurality of hollow fibers; and a second polymer layer of the membrane, wherein the first polymer layer is adjacent to the second polymer layer, wherein the second polymer layer is configured to substantially prevent diffusion of the extracted hydrogen gas into the wastewater stream.

* * * * *

UNITED STATES PATENT AND TRADEMARK OFFICE
CERTIFICATE OF CORRECTION

PATENT NO. : 9,534,236 B2
APPLICATION NO. : 14/198104
DATED : January 3, 2017
INVENTOR(S) : Novak et al.

It is certified that error appears in the above-identified patent and that said Letters Patent is hereby corrected as shown below:

On the Title Page

In Column 2, under "Foreign Patent Documents", Line 1, delete "1715182SA" and insert --1715182A-- therefor On page 2, in Column 2, under "Other Publications", Line 14, delete "Jun. 26, 2015"," and insert --Jan. 26, 2015",-- therefor On page 2, in Column 2, under "Other Publications", Line 25, delete "Wrftten" and insert --Written-- therefor On page 2, in Column 2, under "Other Publications", Line 32, delete "PCT/U820121063960," and insert --PCT/US2012/063960,-- therefor On page 2, in Column 2, under "Other Publications", Line 55, delete "Matrixes"," and insert --Matrices",-- therefor On page 2, in Column 2, under "Other Publications", Line 63, delete "Eledtrospinning" and insert --Electrospinning-- therefor On page 3, in Column 1, under "Other Publications", Line 18, delete ""Electrospining" and insert --"Electrospinning-- therefor On page 3, in Column 2, under "Other Publications", Line 22, delete "nanofibres"," and insert --nanofibers",-- therefor On page 3, in Column 2, under "Other Publications", Line 28, delete "colomn" and insert --column-- therefor Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

In the Specification

In Column 5, Line 9, after "third layer", delete "24." and insert --26.--

In the Claims

In Column 11, Line 5, in Claim 6, delete "material" and insert --material,-- therefor